(12) United States Patent
Lord et al.

(10) Patent No.: US 11,559,077 B2
(45) Date of Patent: Jan. 24, 2023

(54) CARRIER FOR A FUNCTIONAL COMPONENT FOR USE IN MIXING AN AEROSOL PRECURSOR LIQUID, AND ASSOCIATED APPARATUS AND METHOD

(71) Applicant: Nerudia Limited, Liverpool (GB)

(72) Inventors: Chris Lord, Liverpool (GB); David Newns, Liverpool (GB); David Jones, Liverpool (GB)

(73) Assignee: Nerudia Limited, Liverpool (GB)

( * ) Notice: Subject to any disclaimer, the term of this patent is extended or adjusted under 35 U.S.C. 154(b) by 586 days.

(21) Appl. No.: 16/603,481

(22) PCT Filed: Apr. 6, 2018

(86) PCT No.: PCT/EP2018/058901
§ 371 (c)(1),
(2) Date: Oct. 7, 2019

(87) PCT Pub. No.: WO2018/185308
PCT Pub. Date: Oct. 11, 2018

(65) Prior Publication Data
US 2020/0164165 A1   May 28, 2020

(30) Foreign Application Priority Data

Apr. 7, 2017  (GB) .................................... 1705693
Sep. 19, 2017 (GB) .................................... 1715075

(51) Int. Cl.
*A24F 13/00*   (2006.01)
*A24F 17/00*   (2006.01)
(Continued)

(52) U.S. Cl.
CPC ............ *A24B 15/165* (2013.01); *A24F 40/00* (2020.01); *A24F 40/42* (2020.01); *A61M 11/042* (2014.02);
(Continued)

(58) Field of Classification Search
CPC ... A24B 15/165; A24B 15/167; A24F 15/015; A24F 40/00; A24F 40/10; A24F 40/42;
(Continued)

(56) References Cited

U.S. PATENT DOCUMENTS 4,717,016 A * 1/1988 Dalgleish ............. A47G 21/183
                                                426/77
7,170,040 B1 * 1/2007 Benim ................ B65D 81/3461
                                                219/730
(Continued)

FOREIGN PATENT DOCUMENTS

EP     2786664        10/2014
JP     2004528035 A    9/2004
(Continued)

OTHER PUBLICATIONS

GB Search Report for GB1705693.8 dated Feb. 19, 2018; pp. 1-7.
(Continued)

*Primary Examiner* — Abdullah A Riyami
*Assistant Examiner* — Thang H Nguyen
(74) *Attorney, Agent, or Firm* — J. Miguel Hernandez; James R. Gourley; Carstens, Allen & Gourley, LLP (57) ABSTRACT

A carrier, apparatus and method for making an aerosol precursor liquid suitable for aerosolized del cause the medium to release the functional component into said fluid to form an aerosol precursor liquid infused with the functional component. A receptacle comprising a chamber for the carrier is provided for mixing the aerosol precursor liquid. Example functional components include nicotine and nicotine salts.

29 Claims, 4 Drawing Sheets (51) Int. Cl.

| | | |
|---|---|---|
| A24F 25/00 | (2006.01) | |
| A24B 15/16 | (2020.01) | |
| A61M 11/04 | (2006.01) | |
| A61M 15/06 | (2006.01) | |
| A24F 40/00 | (2020.01) | |
| A24F 40/42 | (2020.01) | |
| A61M 15/00 | (2006.01) | |
| A24B 15/167 | (2020.01) | |
| A61M 16/00 | (2006.01) | |
| A24F 15/015 | (2020.01) | |
| A24F 40/10 | (2020.01) | |

(52) U.S. Cl.
CPC ........... *A61M 15/06* (2013.01); *A24B 15/167* (2016.11); *A24F 15/015* (2020.01); *A24F 40/10* (2020.01); *A61M 15/0021* (2014.02); *A61M 2016/0027* (2013.01); *A61M 2205/3368* (2013.01)

(58) Field of Classification Search
CPC ........... A61M 11/042; A61M 15/0021; A61M 15/06; A61M 2016/0027; A61M 2205/3368
See application file for complete search history.

(56) References Cited

U.S. PATENT DOCUMENTS

| | | | | |
|---|---|---|---|---|
| 10,701,976 B2* | 7/2020 | Verleur | ............... | A61M 15/06 |
| 10,856,573 B2* | 12/2020 | Pijnenburg | ............... | A24F 40/53 |
| 2011/0036365 A1* | 2/2011 | Chong | ............... | A24B 15/18 |
| | | | | 131/306 |
| 2015/0040930 A1* | 2/2015 | Robinson | ............... | A24D 1/20 |
| | | | | 131/329 |
| 2015/0068544 A1* | 3/2015 | Moldoveanu | ............... | A24B 15/10 |
| | | | | 131/352 |
| 2016/0050976 A1* | 2/2016 | Righetti | ............... | A24B 15/167 |
| | | | | 206/265 |
| 2016/0073677 A1* | 3/2016 | Kappel | ............... | A24B 15/16 |
| | | | | 206/260 |
| 2016/0073695 A1* | 3/2016 | Sears | ............... | H05B 3/46 |
| | | | | 131/329 |
| 2016/0192703 A1* | 7/2016 | Sebastian | ............... | A24F 23/02 |
| | | | | 131/352 |
| 2016/0235120 A1 | 8/2016 | Liu | | |
| 2017/0065000 A1* | 3/2017 | Sears | ............... | A24D 3/061 |
| 2017/0071249 A1* | 3/2017 | Ampolini | ............... | A61M 11/042 |
| 2021/0008303 A1* | 1/2021 | Bahl | ............... | A61M 11/042 |
| 2022/0030928 A1* | 2/2022 | Chapman | ............... | A61K 31/375 |

FOREIGN PATENT DOCUMENTS

| | | |
|---|---|---|
| JP | 2006511566 A | 4/2006 |
| JP | 2008538911 A | 11/2008 |
| JP | 2009508523 A | 3/2009 |
| JP | 2013-13394 A | 1/2013 |
| JP | WO2012070107 | 5/2014 |
| JP | 2014530633 A | 11/2014 |
| WO | 2016096927 | 6/2016 |
| WO | WO-2016171997 A2 * | 10/2016 |

OTHER PUBLICATIONS

GB Search Report for GB1715075.6 dated Mar. 7, 2018; pp. 1-8.
PCT International Search Report for PCT/EP2018/058901 dated Oct. 11, 2018; pp. 1-7.
Wikipedia; Tobacco Products; https://en.wikipedia.org/w/index.php?title=Tobacco_products&oldid=773635595; pp. 1-11.

* cited by examiner

CARRIER FOR A FUNCTIONAL COMPONENT FOR USE IN MIXING AN AEROSOL PRECURSOR LIQUID, AND ASSOCIATED APPARATUS AND METHOD

CROSS-REFERENCE TO RELATED APPLICATIONS

This application is a US 371 Application from PCT/EP2018/058901 Apr. 6, 2018, which claims priority to GB Application 1705693.8 filed Apr. 7, 2017 and GB Application 1715075.6 filed Sep. 19, 2017, the technical disclosures of which are hereby incorporated herein by reference.

FIELD OF THE INVENTION

The present invention relates to a carrier, apparatus and method for making a composition (hereinafter "aerosol precursor") for aerosol delivery, and more particularly to a carrier, apparatus and method for making an aerosol precursor for disposable cartridges or refilling the reservoir for an aerosol delivery device (such as electronic cigarettes).

BACKGROUND TO THE INVENTION

Combustion of organic material such as tobacco is known to produce tar and other potentially harmful by-products.

Aerosol delivery devices fall into two broad categories: powered and non-powered. In both categories, such devices may comprise electronic systems that permit a user to simulate the act of smoking by producing an aerosol that is drawn into the lungs through the mouth (inhaled) and then exhaled. The inhaled aerosol typically bears nicotine and/or flavourings without, or with fewer of, the odour and health risks associated with traditional combustible smoking and tobacco products. In use, such systems are intended to provide a substitute for the rituals of smoking, whilst providing the user with a similar experience and satisfaction to those experienced in using such traditional smoking and tobacco products.

Devices in the first category may in turn fall into subcategories.

In the first powered sub-category, devices typically use heat and/or ultrasonic agitation to aerosolize an aerosol precursor that comprises tobacco-derived nicotine and/or flavouring, propylene glycol and/or glycerine-based base into an aerosol mist or vapour for inhalation.

Both sub-categories of the first category of device aerosolize an aerosol precursor (known as an "e-liquid" or "e-juice"). Typically, the aerosol precursor is either provided in a premixed form in a dispenser such as an eye dropper bottle into an integral reservoir or into a refillable and/or disposable cartridge that may be removable cartridge. The electronic cigarette is operative to heat and/or ultrasonically agitate the aerosol precursor to produce an aerosol within a constrained fluid stream. The form of the aerosol precursor is such as to allow functional components to be released into a fluid stream passing around or through the reservoir. This process is known as aerosolization and/or atomization.

Aerosolization is the process or act of converting a physical substance into the form of particles small and light enough to be carried on the air (i.e. into an aerosol). Atomization is the process or act of separating or reducing a physical substance into fine particles (i.e. atoms).

The formulation of the aerosol precursor usually comprises excipients such as solvents, thickening agents, stabilizing agents, flavourings, taste regulators and/or active or functional components (hereinafter "functional components") such as nicotine. However, the main ingredients of the aerosol precursor are usually a mix of propylene glycol (PG), vegetable glycerine (VG), and/or polyethylene glycol (PEG), sometimes with differing levels of alcohol mixed with concentrated or extracted natural or synthetic flavourings; and a variable concentration of nicotine. The primary function of the aerosol precursor is to provide an easily handled and stored medium from which it is possible to generate an aerosol and deliver nicotine and/or other functional components. Consequently, the aerosol precursor may be provided in a liquid, gel or other state.

Most commonly the aerosol precursor comprises propylene glycol (PG) and vegetable glycerine (VG) together with a number of other ingredients. Both propylene glycol (PG) and vegetable glycerine (VG) have the property that they may be readily aerosolized at a relatively low temperature (approximately 60° C.) whilst also forming an aerosol mist that resembles tobacco smoke. Although propylene glycol (PG), vegetable glycerine (VG), polyethylene glycol (PEG), and flavourings used in such aerosol precursors are all generally accepted as safe for human consumption, this acceptance is for ingestion and absorption through the stomach at ambient or body temperature (in range 10° C.-35° C.). When used in an aerosol precursor for use in an aerosol delivery device such as an electronic cigarette, the aerosol precursor is heated to relatively high temperatures (typically in the range 150° C.-250° C.). In the case of polyethylene glycol (PEG) which is commonly used in aerosol precursor formulations originating from China, poorly distributed molecules of PEG may result in contaminants as the aerosol precursor is heated sometimes to boiling point. In addition certain flavourings are known to be volatile, sensitive to heat, and/or readily react with other ingredients commonly used in aerosol precursors, including nicotine. Accordingly, there is a general lack of awareness about the long-term effects of consuming certain ingredients when absorbed through the lungs and alveoli.

These effects are thought to be exacerbated by the delivery technology (i.e. aerosol delivery devices). Consumers can now choose from a vast range of aerosol delivery devices with a variety of operating parameters. Many models are cheaply constructed and do not accurately and consistently control parameters such as temperature, whilst others permit users to vary the temperature to produce more/less aerosol mist. For example, higher temperatures may result in accidental burning and/or polymerisation of solvents in the aerosol precursor and create contaminants such as formaldehyde and acrolein (as exemplified in recent analysis which demonstrated that contaminant may be present in concentrations that are undetectable to taste and smell but still harmful to the user). Recent scientific publications report that burning can also result from frequent temperature cycles as the aerosol precursor is rapidly heated and cooled in use which is believed to cause side-reactions in the formulation. In addition some flavour components are believed to detrimentally react with other functional components over time, and are also particularly susceptible to burning if not carefully balanced with certain excipients in the formulation of the aerosol precursor.

In the second powered sub-category, devices typically heat or warm tobacco material rather than combusting the tobacco material as with traditional combustible smoking and tobacco products. During use, direct contact between the heat source and the tobacco material causes moisture in such tobacco material to be released as an aerosol. In addition, volatile compounds may also be released from the tobacco by heat transfer from a heat source and these compounds are entrained with air drawn through the device and inhaled by the user. As the aerosol containing the released compounds passes through the device from an inlet to the mouthpiece (outlet), it cools and condenses to form an aerosol for inhalation by the user. In such devices, heating as opposed to burning, the tobacco material is believed to cause fewer, or smaller quantities, of the more harmful compounds to be released and consequently mat reduce the odour and/or health risks that can arise through combustion and pyrolytic degradation of tobacco.

Aerosol delivery devices falling in the second sub-category of powered devices typically comprise a powered unit that comprises a heating element, into which a tobacco stick resembling and structurally similar to a traditional cigarette is inserted (see for example the iQos® device marketed by Philip Morris International). The stick is generally cylindrical in form with a "mouthpiece" at one end through which the user can draw aerosol for inhalation, and comprising a quantity of axially folded reconstituted tobacco sheet. The heating element penetrates into an end of the stick remote from the mouthpiece between two folds of the tobacco sheet and directly contacts the tobacco within the stick. The sticks are typically disposable and replaceable. Examples of a tobacco sachets for use in a tobacco vaporiser are provided in WO 2016/096927 (Philip Morris Products S.A.), US 2015/0040930 (R.J. Reynolds Tobacco Company) and WO2016/171997 (Paul Viriyapanthu).

A drawback associated with aerosol delivery devices falling in the second sub-category of powered devices may arise due to the heating of tobacco. Whilst the health risks to users of aerosol delivery devices may be lessened somewhat compared to the use of traditional smoking and tobacco products, potentially harmful by-products may still be released during the heating of tobacco and some of the health risks may remain.

A further potential drawback may arise with aerosol delivery devices falling in the second sub-category of powered devices due to the arrangement of the tobacco around the heating element in the device. As a consequence it may not be possible to achieve uniform heating of the tobacco across the full width and along full length of the tobacco sheet, due to the decreasing temperature gradient away from the heating element. For clarity, the tobacco material in folds of the tobacco sheet that are in direct contact with the heating element will be heated by a greater amount than tobacco material comprised in folds of the tobacco sheet that are radially or axially distant from the heating element. This is because tobacco material is thermally insulating and so to ensure that sufficient quantities of volatile compounds are released from the tobacco material to satisfy the user, the heating element must be heated to a temperature sufficient to cause outer folds of the tobacco sheet to release volatile compounds. Consequently, tobacco material in folds closer to the heating element may be overheated causing them to burn and/or cause pyrolysis.

Therefore, although use of aerosol delivery devices of the second sub-category of powered devices may have fewer associated health risks than the use of traditional smoking and tobacco products, the health risks may be greater than those experienced through use of devices of the first sub-category of aerosol delivery devices. However, aerosol delivery devices of the second sub-category of powered devices may be preferable to the user over those of the first sub-category of powered devices as some users perceive physical sensation, satisfaction and experience that more closely simulates those experienced using traditional smoking and tobacco products. These similarities may be experienced due to the user inhaling a warmed aerosol resulting from the tobacco, but also because they are inhaling an aerosol comprising compounds released directly from tobacco material rather than a reproduction or simulation of key compounds as are comprised in the aerosol precursor that is aerosolized by devices of the first sub-category of powered aerosol delivery devices.

Accordingly, there is a need for an aerosol delivery device from the first sub-category of powered devices that provides the user with the physical sensation, satisfaction and experience that more closely simulates those experienced using traditional smoking and tobacco products whilst providing a lessened health risks associated with use of aerosol delivery devices falling in the first sub-category.

It is also an object of the present invention to provide a fluid suitable for delivery by an aerosol generating device.

SUMMARY OF THE INVENTION

According to a first aspect of the invention, there is provided a carrier for a functional component for use in an aerosol generating device, wherein the carrier is fluid permeable and comprises: a tobacco-derived medium for carrying said functional component, the medium being configured to release said functional component into a fluid to provide an aerosol precursor liquid infused with said functional component which is suitable for aerosolized delivery by said aerosol generating device.

Optionally, the medium is configured to release said functional component into said fluid responsive to the presence of said fluid.

Optionally, the medium is configured to release said functional component into said fluid to form a solution.

Optionally, the carrier is in the form of a tablet, gel, capsule, cartridge, pod or pouch. The tobacco-derived medium is typically retained within such a carrier. The carrier is fluid permeable to enable the tobacco-derived medium to come in to contact with fluid in order to infuse it with functional component.

Optionally, the medium is fluid permeable.

Optionally, the functional component is substantially evenly distributed within the medium.

Optionally, the medium comprises tobacco.

Optionally, the tobacco is in the form of tobacco leaf, tobacco stem, tobacco powder, or tobacco dust.

Optionally, the tobacco is in the form of a reconstituted sheet.

Optionally, the functional component comprises nicotine or a nicotine salt.

Optionally, the nicotine salt is selected from a group consisting of: nicotine hydrochloride, nicotine dihydrochloride, nicotine monotartrate, nicotine bitartrate, nicotine bitartrate dihydrate, nicotine sulphate, nicotine zinc chloride monohydrate and nicotine salicylate, and mixtures thereof.

Optionally, the functional component comprises a pH-adjusting agent.

Optionally, the pH-adjusting agent is selected from a group consisting of: carbonates including monocarbonate, bicarbonate and sesquicarbonate, acetates, glycinates, gluconates, borates, glycerophosphates or citrates of alkaline metals or ammonium, phosphate systems including monohydrogenphosphate, dihydrogenphosphate and trihydrogenphosphate, metal hydroxides such as sodium hydroxide and potassium hydroxide, and mixtures thereof.

Optionally, the medium is enclosed in a fluid soluble film or membrane.

Optionally, the fluid soluble film is selected from a group consisting of: Polyester woven mesh, PVA mesh, Nylon, filter paper, silk, Hemp, PVC, PP, Cotton. It will be appreciated that these films are examples of suitable of films, and that other films are equally possible.

Optionally, the medium comprises a filler.

Optionally, the filler is selected from a group consisting of: tobacco dust, cellulose, any plant matter (i.e tobacco stems), Sugar, Foam, porous matrix (desiccant/beads), polysaccharides, polyols, sugars, natural fibres, microcrystalline cellulose, cellulose and cellulose derivatives. It will be appreciated that these fillers are examples of suitable fillers, and that other fillers are equally possible. The term "filler" is intended to mean a material that increase the volume of the medium.

Optionally, the functional component comprises a flavouring.

Optionally, the flavouring is selected from a group consisting of: Mild Menthol, Mixed Berry, Cool Menthol, Peach, Cream Cake, Melon Medley, Apple, Shisha Grape, Virginia Tobacco, American Blend Red. It will be appreciated that these flavourings are examples of suitable of flavourings, and that other flavourings are equally possible.

According to a second aspect of the invention, there is provided a method for mixing an aerosol precursor liquid for aerosolized delivery of a functional component by an aerosol delivery device is provided, the method comprising the steps of: bringing a tobacco-derived medium comprising said functional component into contact with fluid; and allowing the fluid to saturate the medium to thereby cause the medium to release the functional component into said fluid to form a liquid infused with the functional component for use in the aerosol delivery device. Typically the fluid is in the form of a liquid.

Preferably the aerosol precursor liquid comprises a solution of the functional component.

Optionally, the method further comprising a step of agitating the medium in the fluid.

Optionally, the step of agitating the medium comprises shaking a receptacle comprising the medium and the fluid.

Optionally, the step of bringing the medium into contact with the fluid comprises introducing said medium into a receptacle holding said fluid.

Optionally, the step of bringing the medium into contact with the fluid comprises introducing said fluid into a receptacle holding said medium.

Optionally, the method further comprises the step of: introducing an agitation member into a receptacle before performing the step of agitating the medium in the fluid.

Optionally, the method further comprises the step of refilling a reservoir of an aerosol delivery device with the liquid infused with the functional component.

Typically, in the method the step of refilling the reservoir does not include a step of supplying the carrier to the reservoir.

According to a third aspect, a receptacle for mixing a solution for use in an aerosol delivery device is provided, the receptacle comprising a chamber for receiving a carrier according to the first aspect. Optionally a receptacle contains a carrier according to the first aspect, wherein the receptacle is purged of air.

According to a fourth aspect, an aerosol delivery device comprising a receptacle according to the third aspect is provided.

Optionally, the receptacle is configured to be removably coupled to said device.

Embodiments of the first aspect of the invention include a composition for use in aerosol delivery device that comprises fibrous organic plant material or a plant extract that is retained within a pouch in a similar arrangement to that used in tea bags. In a particularly preferred embodiment of the first aspect of the invention a carrier in the form of shredded leaf tobacco is provided, the carrier being provided in the form of a fluid permeable pouch is which the medium (tobacco) is retained. When the medium comes into contact with a fluid, the fluid soaks into the medium and causes it to release certain volatile components including desirable functional components such as, for example, nicotine and flavonoids. Consequently, these volatile components will 'infuse' into the fluid. The resulting composition is suitable for aerosolized delivery by an aerosol delivery device of the type described in connection with first sub-category of powered devices above.

The medium of the invention, may be for example organic material selected from the group consisting of: tobacco, fruits, herbs, medicinal plants (including *cannabis*), tea, vegetables, spices, and organic filling and bulking agents and mixtures thereof, such as, for example, mixtures of tobacco, herbs, and/or spices. The medium will include at least some material which is derived from tobacco.

Although the particularly preferred embodiment describes the invention with a carrier in the form of a pouch, alternative structures include, but are not limited to tablets pressed from the medium, gels in which plant material is suspended, and capsules, cartridges or pods in which the plant material is encapsulated. In relation to all of the foregoing carrier structures the skilled person will appreciate that the intent of the invention is that the medium comes into contact with the fluid to permit a composition to be formed. Accordingly, it will be appreciated that the aims of the invention may be achieved with carrier configurations facilitating contact between a large proportion of the medium, retaining loose plant material within a fluid permeable structure, and/or encapsulating the medium within a frangible or dissolvable encapsulation material.

In all embodiments of the invention the carrier will be fluid permeable, and it is preferred that any functional component is evenly distributed within the medium to ensure optimum release into the fluid.

A particularly preferred embodiment comprises a medium that includes tobacco preferably in the form of tobacco leaf, tobacco stem, tobacco powder, or tobacco dust. Ideally the tobacco is shredded leaf or stem, but tobacco in the form of a reconstituted sheet of shredded, powdered tobacco or tobacco dust also falls within the teachings of the invention.

As the invention is intended primarily to be used in connection with smoking cessation, a particularly preferred functional component comprised in the medium is nicotine. Nicotine is found naturally in tobacco plant material and the selection of a plant material from a particular variety of the tobacco plant may result in sufficient nicotine being released into the fluid.

Alternatively, in some embodiments a nicotine salt may be added either to the tobacco plant material or to a filler material. Examples of suitable nicotine salts include:
nicotine hydrochloride,
nicotine dihydrochloride,
nicotine monotartrate,
nicotine bitartrate,
nicotine bitartrate dihydrate,
nicotine sulphate,
nicotine zinc chloride monohydrate
and nicotine salicylate, and mixtures thereof.

To promote user compliance and aid absorption, a pH-adjusting agent may be added to the medium. Examples of Suitable pH-adjusting agents include:

carbonates including monocarbonate, bicarbonate and sesquicarbonate,
   acetates,
   glycinates,
   gluconates,
   borates,
   glycerophosphates or citrates of alkaline metals or ammonium,
phosphate systems including monohydrogenphosphate, dihydrogenphosphate and trihydrogenphosphate,
metal hydroxides such as sodium hydroxide and potassium hydroxide, and mixtures thereof.

The medium may be enclosed in a fluid soluble film or membrane. The fluid soluble film may be selected from a group consisting of: Polyester woven mesh, PVA mesh, Nylon, filter paper, silk, Hemp, PVC, PP, Cotton.

The functional component may also include a flavouring. The flavouring may be selected from a group consisting of: Mild Menthol, Mixed Berry, Cool Menthol, Peach, Cream Cake, Melon Medley, Apple, Shisha Grape, Virginia Tobacco, American Blend Red.

BRIEF DESCRIPTION OF THE DRAWINGS

A complete understanding of preferred embodiments of the present invention may be obtained by reference to the accompanying drawings, when considered in conjunction with the subsequent, detailed description, provided by way of example only and in which.

DETAILED DESCRIPTION OF THE DRAWINGS

Before the invention is described in further detail, it is to be understood that the invention is not limited to the particular embodiments described, as such may, of course, vary. It is to be understood that the terminology used herein is for the purpose of describing particular embodiments only, and not intended to be limiting, since the scope of the present invention will be limited by the appended claims.

Unless defined otherwise, all technical and scientific terms used herein have the same meaning as commonly understood by one of ordinary skill in the art to which this invention belongs or as determined by the context in which such terms are used. Although any methods and materials similar or equivalent to those described herein can also be used in the practise or testing of the present invention, a limited number of exemplary methods and materials are described herein.

It must be noted that as used herein and in the appended claims, the singular forms of "a", "an", and "the" include plural referents unless the context clearly dictates otherwise.

All publications mentioned herein are incorporated herein by reference to disclose and describe the methods and materials in connection with which the publications are cited. The publications discussed herein are provided solely for their disclosure prior to the filing date of the present patent application. Nothing herein is to be construed as an admission that the present invention is not entitled to antedate such publication by virtue of prior invention. Further, if dates of publication are provided, they may be different from actual publication dates and may need to be confirmed independently.

The disclosure herein is directed to a carrier for functional components for making an aerosol precursor for an aerosol-generating device, together with the apparatus and methods for producing such aerosol precursor, and has applicability to the filling and refilling of refillable fluid reservoirs of such aerosol-generating devices with an aerosol precursor together with the making of such aerosol precursor.

Figure 1:
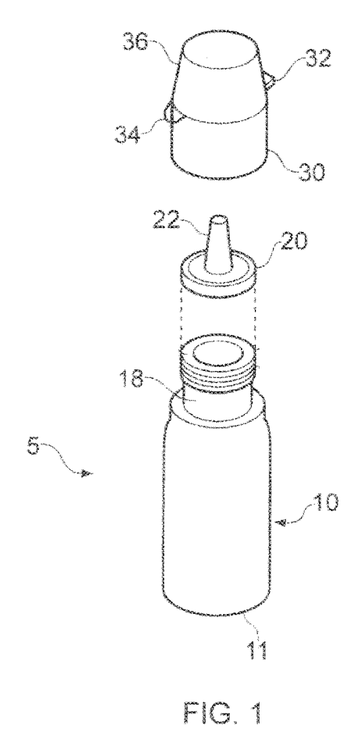
FIG. 1 is an exploded perspective view illustration showing a prior art fluid dispenser of the type typically used for refilling the reservoir of an aerosol-generating device.

FIG. 1 is shows an eyedropper type liquid dispenser 5 of the type presently used for refilling aerosol-delivery devices. The liquid dispenser 5 includes a container 10, a dispensing portion 20 that comprises a liquid-dispensing tip 22, and a cap portion 30 that may be integrally formed with the neck portion 18 of the dispenser 10, the dispensing portion 20, or may be removable. As illustrated in FIG. 1, the cap portion 30 is removable and has a hinged portion 32 for permitting the lid portion 36 to be opened about the hinge portion 32 to expose the liquid-dispensing tip 22. Also illustrated is projection 34 which is provided to facilitate easy opening of the lid portion 36 by the user and when in the closed position prevents leakage from the liquid-dispensing tip 22.

Figure 2:
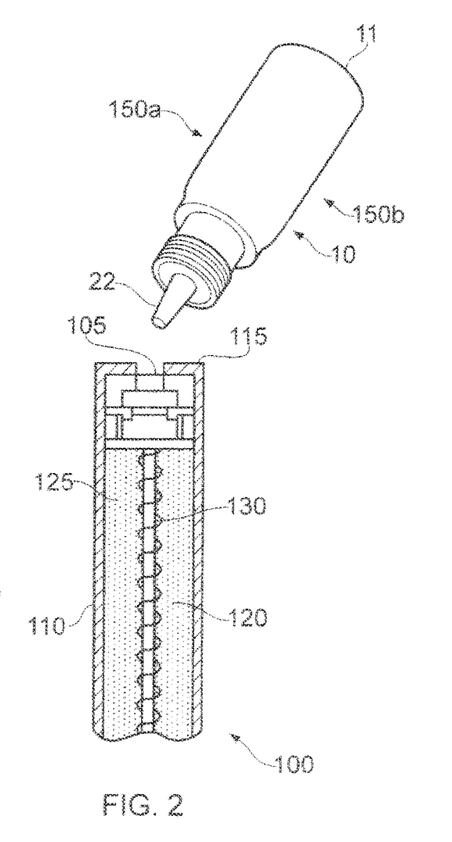
FIG. 2 is a an exploded perspective view illustration showing a fluid dispenser of the type described in connection with FIG. 1 being used to dispense liquid into the reservoir of an aerosol-generating device.
Figure 3:
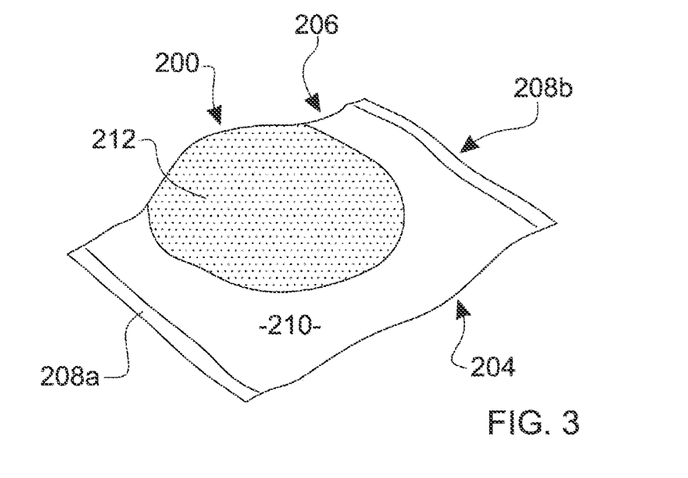
FIG. 3 is shows a perspective view of a carrier in accordance with the teachings of the present invention.
Figure 4:
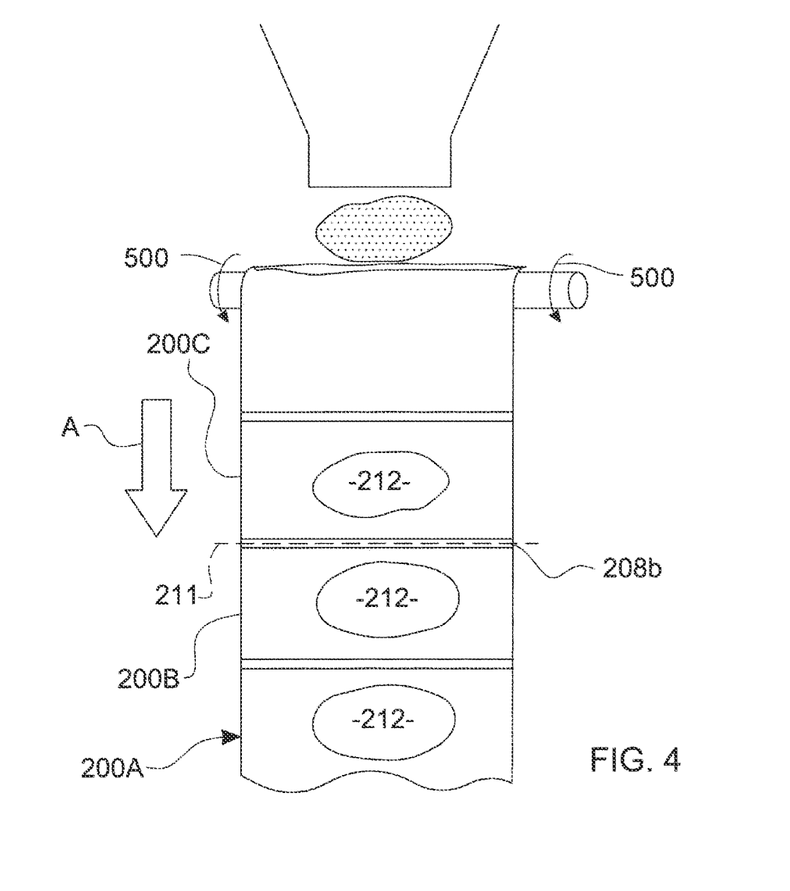
FIG. 4 is an illustrative view of a manufacturing process for producing pouches for use in accordance with the present invention.
Figure 5A:
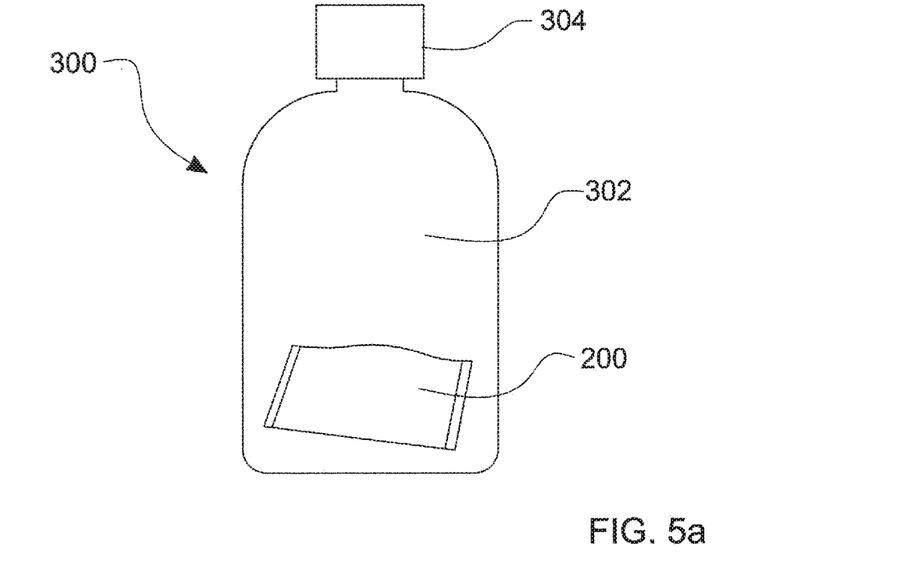
FIGS. 5a, 5b, and 5c show the steps undertaken to form a solution including a functional component in accordance with the present invention.
Figure 5B:
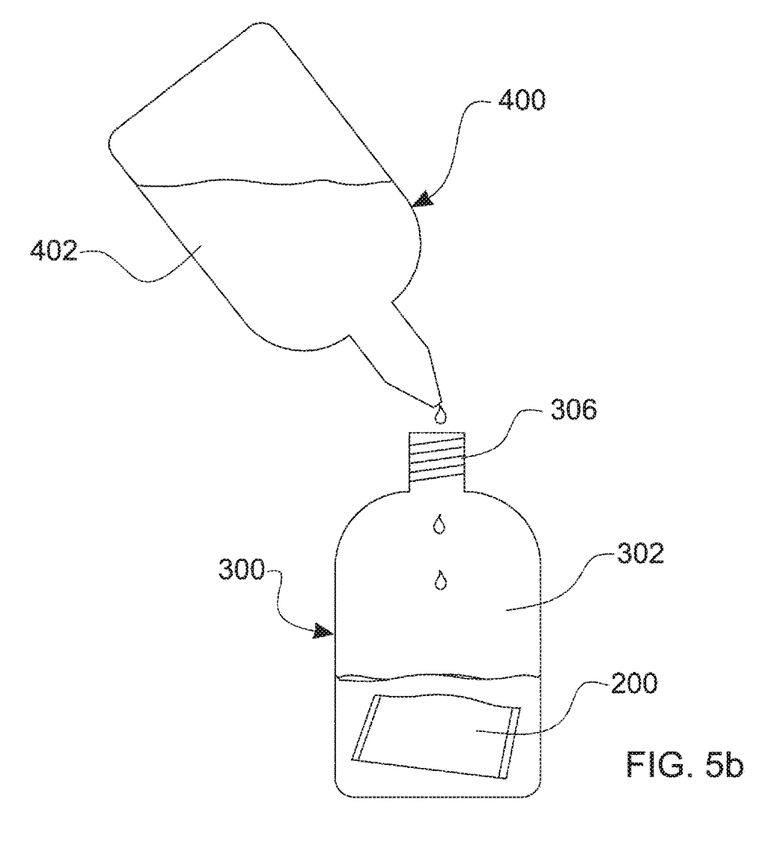
Figure 5C:
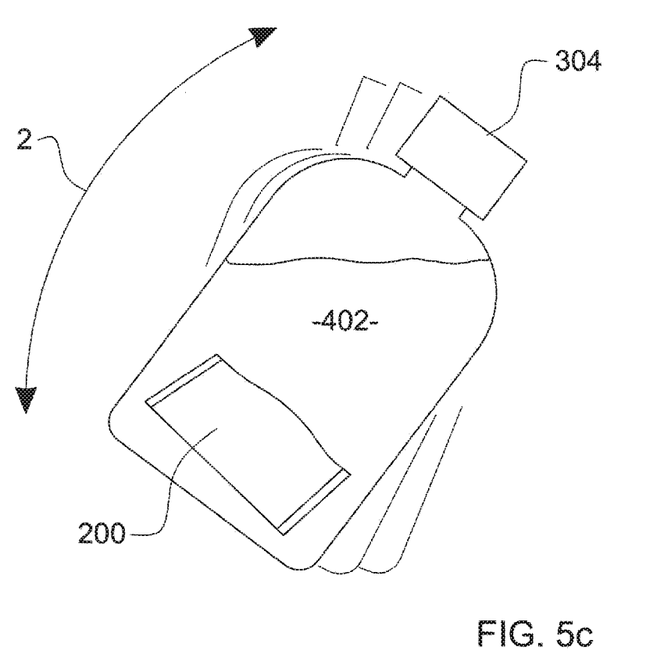

Referring now to FIG. 2, a liquid dispenser 10 of the type described in relation to FIG. 1 is shown, together with a cross-sectional view of a portion of the body 110 of an aerosol-delivery device 100 in which a reservoir 120 for liquid is located. The aerosol-delivery device 100 illustrated in FIG. 2 is of a type where access to the reservoir 120 is integrally formed with the aerosolization chamber. Thus, the reservoir 120 is typically located in the proximal end 115 of the mouthpiece (not shown) and comprises a coiled heating element 130.

The reservoir 120 contains wicking material 125 for transferring liquid held in the chamber into engagement with the coiled heating element 130. The outer walls of the reservoir 120 are typically formed from a plastic material such as high-density polypropylene.

Before attempting to refill the aerosol-delivery device 100 the user must first remove the mouthpiece to provide access to inlet aperture 105 of reservoir 120. The user typically holds the aerosol-delivery device 100 in an orientation in which its proximal end (i.e. the mouthpiece end) is uppermost. The aerosol-delivery device 100 does not necessarily need to be vertical as a slight inclination is possible to facilitate refilling, and indeed a slight inclination can aid refilling as it permits air to more readily enter and replace the volume vacated by the liquid dispensed. However, it has been found that angles greater than around 20 degrees from the vertical can result in spillage.

Refill dispenser is shown held at an angle of approximately 45 degrees from the vertical with the liquid-dispensing tip 22 disposed in the vicinity of the inlet aperture 105 of the aerosol-delivery device so that any droplets expelled therefrom would fall generally in the region of the inlet aperture 105. Users typically find refilling of the reservoir

120 of an aerosol generating device 100 to be easier if the dispenser is held at an angle as their view of the liquid-dispensing tip 22 is not restricted by the body of the dispenser 10.

In use, the user will hold the refill dispenser 10 in an inverted orientation and a droplet of liquid typically forms at the end of the liquid-dispensing tip 22. Any volume in the body of the dispenser 10 that is not filled with liquid is typically air, which naturally rises to the bottom 11 of the dispenser 10 when it is disposed in a substantially inverted orientation. To dispense liquid from the tip 22 the user squeezes the body of the dispenser 10 by applying pressure in the direction of arrows 150*a* and 150*b* causing liquid to be expelled from the tip 22. Furthermore, the walls of the dispenser 10 in the region adjacent to the arrows 150*a* and 150*b* may be inwardly deformed resulting in a reduction of the internal volume of the dispenser 10. Since the dispenser 10 is typically moulded from a resilient plastic material, as the user releases the inwardly directed pressure applied to the walls of the dispenser 10 they return to their normal position. Consequently, as a volume of liquid has been dispensed from the dispenser 10 into the reservoir 120 the vacant volume will be replaced with air drawn through the tip 22.

Liquid aerosol precursor formulations are typically supplied in premixed form in a dispenser such as an eye dropper bottle into an integral reservoir or into a refillable and/or disposable cartridge that may be a removable cartridge. Accordingly, since the precursor is supplied in a premixed form users typically purchase a variety of formulations of favourite flavourings and/or nicotine strengths.

A first embodiment of the present invention will now be described in relation to FIG. 3 which shows a perspective view of an extraction bag or pouch 200. A main body of the pouch 200 has a generally polygonal shape. As shown in FIG. 3 the main body is generally rectangular shape. The main body has a first surface 204 and a second surface 206 and seams 208 formed around the external edges to define a pocket 210 therebetween. A quantity of a medium 212 for carrying one of more functional components is located in the pocket 210.

In the preferred embodiment of the invention that is illustrated in FIG. 3, the main body is formed from a fluid permeable material having a pore size suitable for constraining the bulk material of the medium to be constrained within the pocket 210.

When manufacturing the pouch 200 a sheet of continuous cylindrical material or sleeve is fed in the direction indicated by arrow A in FIG. 4. The sleeve is held vertically and configured so that as the sleeve is fed over rollers 500. The surfaces of the sleeve separate to form the pocket 210 and is sealed along edge 208*a*. The sealing may preferably be achieved by the application of pressure and/or heat.

A measured quantity of the medium 212 is then deposited through the open end 208*b* into the pocket 210 formed between the sealed opposing surfaces 204 and 206. The ratio of the quantity of medium 212 and the dimensions of the pouch 200 are critical as medium that is too tightly packed within the pouch 200 may compromise the subsequent recovery of the nicotine. The surfaces 204 and 206 are sealed along edge 208*b* to constrain the medium 212 within the pocket 210. Finally, once the surfaces are sealed along edge 208*b* the main body is cut away from sheet or sleeve along edge 208*b* and just above the seal. As can be seen from FIG. 4, the seal formed along the upper edge 208*b* of pouch 200*a* forms the lower seal 208*a* of the subsequent pouch 200*b* above. Consequently, the seal 208 between each pouch should be of sufficient thickness to permit the pouches 200*a* and 200*b* to be separated by cutting along the centre of the seal, along the line indicated by dotted line 211 whilst leaving the upper edge 208*b* of pouch 200*a* and lower edge 208*a* of pouch 200*b* sealed. Thus, horizontal sealing and cutting may be simultaneously performed.

Turning now to the medium 212 that is constrained within the pouch 212, in the embodiments of the invention illustrated in FIGS. 3-4, the bulk of the medium 212 therein comprises treated organic tobacco material. For the purposes of the present invention it is immaterial whether the organic tobacco material is leaf or stem, or whether it is in shredded, ground, or powdered form provided that the pores of the material from which the surfaces 204 and 206 of the pouch 200 are formed are dimensioned to constrain the organic tobacco material within the pouch 200.

The form of the organic material is immaterial to the teachings of the present invention other than it should be appropriately dimensioned to fit within the pocket of the pouch 200. In a particularly preferred embodiment of the present invention the organic tobacco material is in the form of dust or powder to provide the optimal surface area. The organic tobacco material is typically pre-treated by grinding before being dried.

According to the teachings of the present invention the organic tobacco material is first washed in purified water to remove contaminants. The process of washing the organic material may also cause the material to swell.

A composition of vegetable glycol and pure liquid nicotine is then added to the organic tobacco material. The vegetable glycol causes the nicotine to be more evenly distributed across the organic tobacco material. The intention is to saturate the organic tobacco material with vegetable glycol rather than nicotine but it also enhances the saturation of the nicotine into the material. The composition is preferably in the ratio 1:3 nicotine to vegetable glycol and is added to 3 parts tobacco material.

The damp organic tobacco material is then deposited in the pouch 200. Each pouch 200 will typically comprise 0.7 g of tobacco material, 0.7 g of vegetable glycol, and 0.24 g of nicotine. However it will be apparent to one of ordinary skill in the art that alternative compositions will be appropriate for different types and forms of organic tobacco material and other fillers.

Once the pouch 200 has been sealed as described in the foregoing description, it is placed within a container 300 which is purged of air with a gas such as argon and sealed to prevent evaporation and degradation.

Referring now to FIGS. 5*a* 5*b*, immediately prior to requiring the aerosol precursor, the user removes the cap 304 from the neck of the container 300 to expose the aperture 306 and to provide access to the chamber 302 through the aperture 306 to the pouch 200 contained therein. A measured volume of fluid 402 is then dispensed from a dispenser 400 through the aperture 306 of container 300 and into the chamber 302. The measured volume of fluid is such that it does not completely fill chamber 302 but leaves a headspace of air above. The cap 304 is then replaced to seal the chamber with both the measured volume of fluid 402 and the pouch 200.

As shown in FIG. 5*c*, next the user shakes the container 300 vigorously for period of 10 seconds, before allowing the container 300 to stand for a period of 10 minutes. Upon expiry of the period of 10 minutes the user then shakes the container for a further period of 10 seconds.

The skilled person will appreciate from the foregoing teachings:

The longer the container 300 is shaken the better.

Alternative embodiments include:

a. An additional container in which the medium is constrained, wherein the additional container is removably engaged into the mouth of the above-described container 300.

b. the pouch 200 being aseptically sealed in a bag or package with a frangible seal.

c. a cafetierre type arrangement which, after shaking, constrains the medium in a portion of the container away from the aperture/opening.

d. a capsule having rupturable ends which are penetrated when the capsule is inserted into the device to permit a fluid stream to pass therebetween and which constrain the medium therein.

e. a tablet or gel of organic material which disintegrates when placed in a fluid.

f. a filter fitted into the aperture of the container 200 or capsule.

In the foregoing description various embodiments of the present invention have been presented for the purpose of illustration and description. They are not intended to be limiting or exhaustive or to limit the scope of the invention to the precise form disclosed. Obvious modifications and alternatives are possible in light of the teachings comprised herein. The various embodiments were chosen and described to provide the best illustrations of the principles of the present invention and their practical implementation, and to enable one of ordinary skill in the art to utilise the various embodiments with various modifications as are suited to the use contemplated. All such modifications and variations are within the scope of the present invention as determined by the appended claims when interpreted in accordance with the breadth they are fairly, legally and equitably entitled.

The invention claimed is:

1. A carrier for a functional component for use in mixing an aerosol precursor liquid for aerosolized delivery by an aerosol generating device, wherein said carrier is fluid permeable and comprises:
    a tobacco-derived medium for carrying said functional component, the medium being constrained within the carrier and configured to release said functional component when contacted with a fluid to provide an aerosol precursor liquid infused with said functional component, the aerosol precursor liquid being suitable for supply to a fluid reservoir of an aerosol generating device for aerosolized delivery by said aerosol generating device.

2. The carrier as claimed in claim 1, wherein the medium comprises tobacco.

3. The carrier as claimed in claim 2, wherein the tobacco is in the form of tobacco leaf, tobacco stem, tobacco powder, or tobacco dust.

4. The carrier as claimed in claim 3, wherein the tobacco is in the form of a reconstituted sheet.

5. The carrier as claimed in claim 1, wherein the functional component comprises nicotine or a nicotine salt.

6. The carrier as claimed in claim 5, wherein the nicotine salt is selected from a group consisting of: nicotine hydrochloride, nicotine dihydrochloride, nicotine monotartrate, nicotine bitartrate, nicotine bitartrate dihydrate, nicotine sulphate, nicotine zinc chloride monohydrate and nicotine salicylate, and mixtures thereof.

7. The carrier as claimed in claim 1, wherein the medium is configured to release said functional component into said fluid responsive to the presence of said fluid.

8. The carrier as claimed in claim 1, wherein the medium is configured to release said functional component into said fluid to form a solution.

9. The carrier as claimed in claim 1, wherein the carrier is in the form of a tablet, gel, capsule, cartridge, pod or pouch.

10. The carrier as claimed in claim 1, wherein the medium is fluid permeable.

11. The carrier as claimed in claim 1, wherein the functional component is substantially evenly distributed within the medium.

12. The carrier as claimed in claim 1, wherein the functional component comprises a pH-adjusting agent.

13. The carrier as claimed in claim 12, wherein the pH-adjusting agent is selected from a group consisting of: carbonates including monocarbonate, bicarbonate and sesquicarbonate, acetates, glycinates, gluconates, borates, glycerophosphates or citrates of alkaline metals or ammonium, phosphate systems including monohydrogenphosphate, dihydrogenphosphate and trihydrogenphosphate, metal hydroxides such as sodium hydroxide and potassium hydroxide, and mixtures thereof.

14. The carrier as claimed in claim 1, wherein the medium is enclosed in a fluid soluble film or membrane.

15. The carrier as claimed in claim 14, wherein the fluid soluble film is selected from a group consisting of: Polyester woven mesh, PVA mesh, Nylon, filter paper, silk, Hemp, PVC, PP, Cotton.

16. The carrier as claimed in claim 1, wherein the medium comprises a filler.

17. The carrier as claimed in claim 16, wherein the filler is selected from a group consisting of: tobacco dust, cellulose, any plant matter (i.e tobacco stems), Sugar, Foam, porous matrix (desiccant/beads), polysaccharides, polyols, sugars, natural fibres, microcrystalline cellulose, cellulose and cellulose derivatives.

18. The carrier as claimed in claim 1, wherein the functional component comprises a flavouring.

19. The carrier as claimed in claim 18, wherein the flavouring is selected from a group consisting of: Mild Menthol, Mixed Berry, Cool Menthol, Peach, Cream Cake, Melon Medley, Apple, Shisha Grape, Virginia Tobacco, American Blend Red.

20. A method for mixing an aerosol precursor liquid for aerosolized delivery of a functional component by an aerosol delivery device, which method comprises the steps of:
    bringing a fluid permeable carrier, which has a tobacco-derived medium which carries said functional component constrained within the fluid permeable carrier, into contact with fluid; and
    allowing the fluid to saturate the medium to thereby cause the medium to release the functional component into said fluid to form a liquid infused with the functional component for use in the aerosol delivery device.

21. The method of claim 20, further comprising the step of agitating the medium in the fluid.

22. The method of claim 21, wherein the step of agitating the medium comprises shaking a receptacle comprising the medium and the fluid.

23. The method of claim 20, wherein the step of bringing the medium into contact with the fluid comprises introducing said medium into a receptacle holding said fluid.

24. The method of claim 20, wherein the step of bringing the medium into contact with the fluid comprises introducing said fluid into a receptacle holding said medium.

25. The method as claimed in claim 21, further comprising the step of: introducing an agitation member into a receptacle before performing the step of agitating the medium in the fluid.

26. The method as claimed in claim 21, further comprising the step of refilling a reservoir of an aerosol generating device with the liquid infused with the functional component.

27. A receptacle for mixing a liquid for use in an aerosol delivery device, which receptacle comprises a chamber containing a carrier as claimed in claim 1.

28. An aerosol delivery device comprising the receptacle as claimed in claim 27.

29. The aerosol delivery device as claimed in claim 28, wherein the receptacle is configured to be removably coupled to said aerosol delivery device.

\* \* \* \* \*